US006702836B2

(12) United States Patent
Fuhr

(10) Patent No.: US 6,702,836 B2
(45) Date of Patent: Mar. 9, 2004

(54) CHIROPRACTIC ADJUSTING INSTRUMENT

(75) Inventor: Arlan W. Fuhr, Phoenix, AZ (US)

(73) Assignee: Activator Methods International, Ltd., Phoenix, AZ (US)

( * ) Notice: Subject to any disclaimer, the term of this patent is extended or adjusted under 35 U.S.C. 154(b) by 0 days.

(21) Appl. No.: 10/079,104

(22) Filed: Feb. 20, 2002

(65) Prior Publication Data

US 2002/0077664 A1 Jun. 20, 2002

Related U.S. Application Data

(62) Division of application No. 09/677,425, filed on Oct. 2, 2000, now Pat. No. 6,379,375.

(51) Int. Cl.[7] .................................................. A61K 1/00

(52) U.S. Cl. ........................ 606/238; 238/601; 238/108

(58) Field of Search ................................ 606/238, 239, 606/237; 601/107, 108, 110, 111

(56) References Cited

U.S. PATENT DOCUMENTS 4,495,940 A * 1/1985 Takaishi ..................... 601/108
4,841,955 A * 6/1989 Evans et al. ................ 601/101

* cited by examiner

*Primary Examiner*—Danton D. Demille
(74) *Attorney, Agent, or Firm*—Leydig, Voit & Mayer, Ltd.

(57) ABSTRACT

An improved chiropractic adjusting instrument is provided for use in spinal manipulative therapy and for exciting a human spine at preselected resettable frequencies within the range of its natural frequency. The improvement comprises a preloaded body contact thrust member.

1 Claim, 3 Drawing Sheets

CHIROPRACTIC ADJUSTING INSTRUMENT

This application is a divisional of pending application Ser. No. 09/677,425, filed Oct. 2, 2000 now U.S. Pat. No. 6,379,375.

BACKGROUND OF THE INVENTION

1. Field of the Invention

The present invention relates generally to the chiropractic adjustment of musculoskeletal structures, and more particularly concerns an improved chiropractic adjusting instrument for use in spinal manipulative therapy. The present invention is a further refinement of the improved instrument described and claimed in U.S. Pat. No. 5,626,615, issued May 6, 1997 of which applicant of the present invention is a co-inventor.

2. Description of the Prior Art

The chiropractic art is generally concerned with adjusting misaligned body structures by manually manipulating the various joints in the human body. Of more specific interest in the art, however, is the spinal column which is comprised of several interconnected musculoskeletal structures or vertebrae. Unlike other, less critical body structures, the spinal column must be treated or manipulated with extreme caution because of its link with the central nervous system.

The human spine is susceptible to many different pathologic abnormalities including misalignment, miscellaneous trauma and pain, and degeneration as a result of age or disease. By employing various physical therapy techniques, though, a chiropractor, or one skilled in the chiropractic art, one may be able to successfully treat a pathologic spine. Successful treatment will not only relieve any pain or discomfort that the patient might be suffering, but will also improve the overall quality of life of that patient.

One common spinal-adjustment technique involves applying thrusts or forces to the afflicted region of the spine. In particular, this technique involves either "mobilizing" the spine (i.e. passively moving the spine with relatively slow cyclic or oscillatory motion), or "manipulating" the spine (i.e. applying an impulsive thrust or force in a well-defined direction to a specific region of the spine). Depending on professional affiliations, this technique is referred to as chiropractic adjustment, osteopathic manipulation, orthopedic manual therapy, and/or spinal manipulative therapy.

There are several well known procedures or techniques for "manipulating" or administering impulsive thrusts to a spine. One technique involves applying one or more rapid thumb thrusts to misaligned or afflicted vertebrae. Thumb thrusts, however, tend to be both imprecise in magnitude and location and tiresome to administer. Another technique involves using a manually operated chiropractic adjusting instrument. For instance, U.S. Pat. No. 4,116,235, issued to Fuhr et al. ("Fuhr") and U.S. Pat. No. 4,498,464, issued to Morgan, Jr., disclose such instruments.

The Fuhr device, in particular, is a manually operated, spring-loaded device for delivering an impact force or thrust to a patient's spine at a rapid speed and in a precise line of drive. Further, although the magnitude of the impact force delivered by the Fuhr device is adjustable, the frequency at which the impact force is delivered is completely arbitrary. As such, the Fuhr device is not mechanically "tuned" to any particular frequency.

The ability to "tune" a chiropractic adjusting instrument to a desired frequency, though, offers the chiropractic clinician several significant advantages over the prior art. For instance, a chiropractic adjusting instrument that is "tuned" or "tunable" to the natural frequency of a human spine maximizes the dynamic motion response of the spine while, at the same time, minimize the magnitude of the requisite impact force. Such a chiropractic adjusting instrument not only enhances the overall effectiveness of spinal manipulative therapy, but would also decrease the possibility of damage to the vertebrae during such treatment. The instrument described and claimed in U.S. Pat. No. 5,626,615 does provide such an instrument which is "tunable" within a broad range of frequencies. As a practical matter, however, it is desirable to have an instrument which may be easily set or settable to the most commonly used and effective frequencies.

OBJECTS AND SUMMARY OF THE INVENTION

The primary object of the present invention is to provide an improved chiropractic adjusting instrument which is "tunable" to and settable to a preselected number of desired frequencies within the optional range of natural frequency.

A more specific object of the present invention is to provide an improved chiropractic adjusting instrument which is "tunable" or settable to the natural frequency of a musculoskeletal structure and may be easily resettable to a selected number of frequencies with a range of suitable frequencies.

An even more specific object of the present invention is to provide an improved chiropractic adjusting instrument which is "tunable" to the natural frequency of a human spine or a selected number of different frequencies or a range of thrusts.

Another object of the present invention is to provide an improved chiropractic adjusting instrument of the foregoing type which is reliable, precise, and convenient to use and readily and reliably resettable.

These and other features and advantages of the invention will become apparent upon reading the following description of a preferred exemplified embodiment of the invention, and upon reference to the accompanying drawings wherein:

While the invention will be described and disclosed in connection with certain preferred embodiment and procedures, it is not intended to limit the invention to the specific embodiment. Rather it is intended to cover all such alternative embodiments and modifications as fall within the spirit and scope of the appended claims.

DETAILED DESCRIPTION OF THE PREFERRED EMBODIMENT

Figure 1:
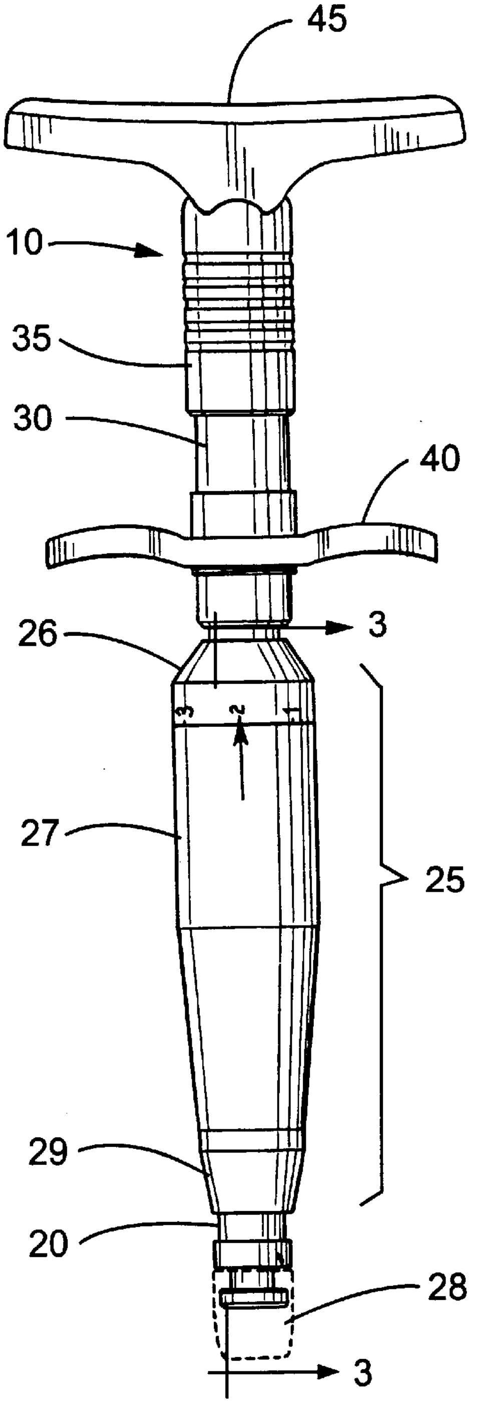
FIG. 1 is a side view of an improved chiropractic adjusting instrument according to the present invention having a shaped mass set in one of a selectable number of desired frequencies.
Figure 2:
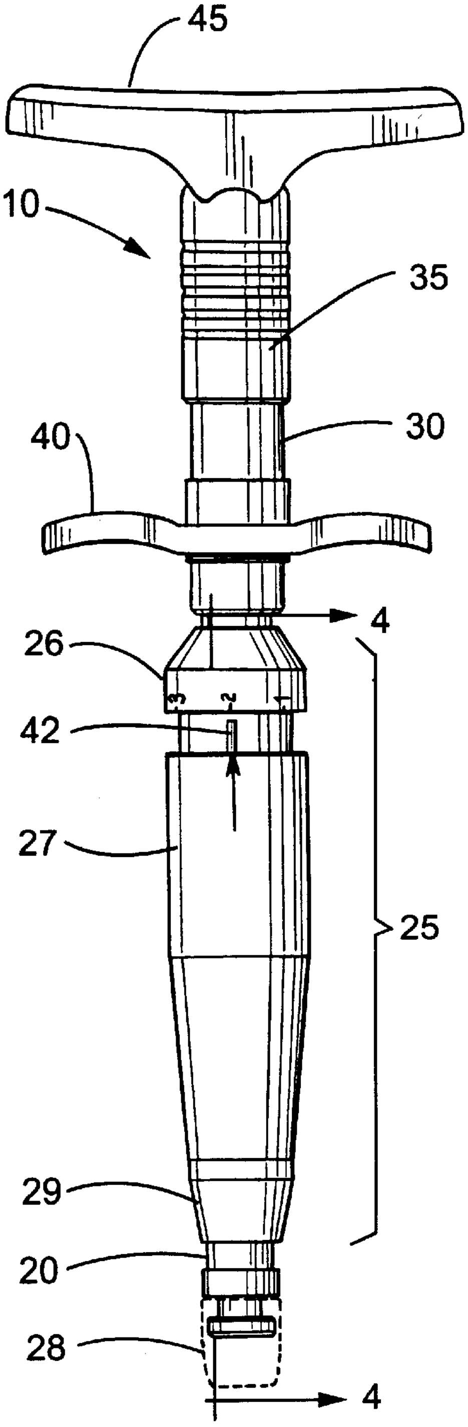
FIG. 2 is a side view of the improved chiropractic adjusting instrument having a shaped mass which has a plurality of settings that mechanically tunes the instrument to a desired frequency or amount of thrust.

Referring to the drawing FIGS. 1 and 2, the instrument as disclosed in U.S. Pat. No. 5,626,615 is a manually operated chiropractic posterior-anterior adjusting instrument 10. It broadly comprises thrust element 20, a shaped mass thrust portion 25, a removable body contact 28, a main body 30, an end cap 35, a first handle member 40, and a second handle member 45. Internally (not shown), a spring means propels the body thrust element outwardly; and a trigger means actuates the spring means to impart a thrust to the thrust element 20.

The device 10 also incorporates a calibration means for controlling the amount that the shank portion of the thrust element 20 retracts within the main body 30 when the first and second handle portions 40, 45 are squeezed together, for controlling the amount of potential energy imposed on the spring means, and, more particularly, for adjusting the amplitude of the input force delivered to the musculoskeletal structure.

In accordance with certain objects of the present invention, the device has been improved such that the input force delivered by the chiropractic adjusting instrument 10 is now "tuned" or is "tunable" to the natural frequency of the musculoskeletal structure being examined and resettable to a number of preselected alternatives which are commonly useable for chiropractic adjustments. These objects are achieved by altering the amount of thrust delivered from the trigger mechanism to the thrust element.

Figure 3:
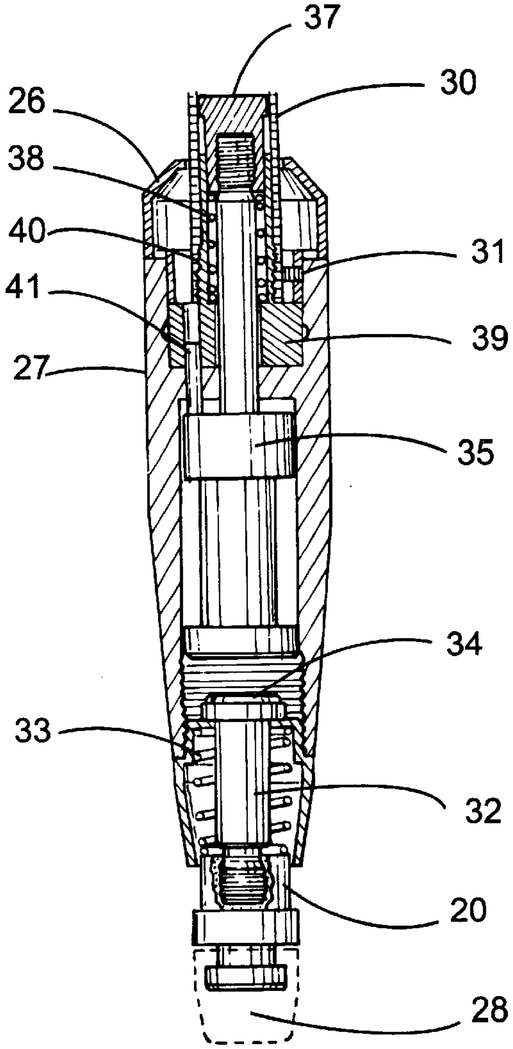
FIG. 3 is a cross-sectional view of the chiropractic adjusting instrument shaped mass portion taken along line 3—3 in FIG. 1.
Figure 4:
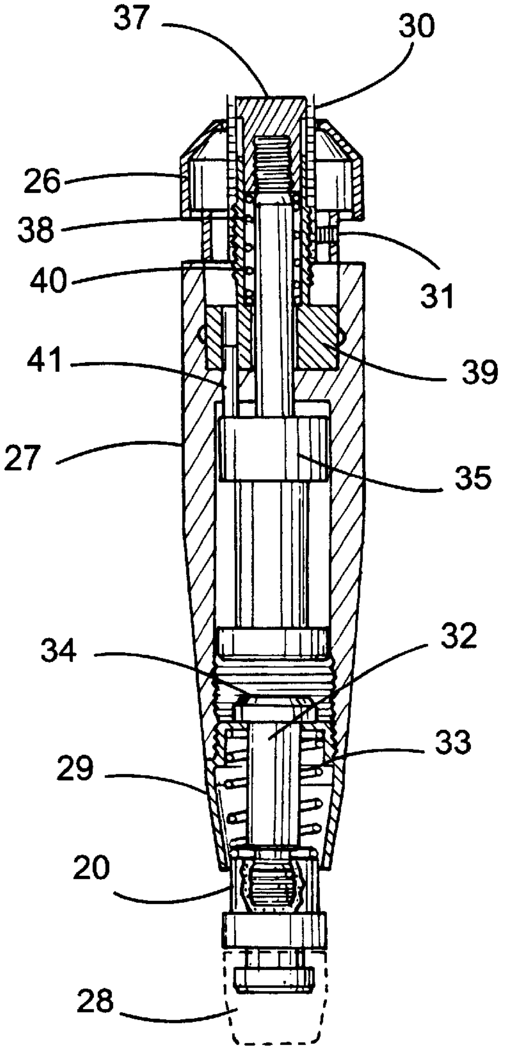
FIG. 4 is a cross-sectional view of the improved chiropractic adjusting instrument shaped mass portion taken along line 4—4 in FIG. 2.

A preferred embodiment of a mechanically tuned chiropractic adjusting instrument 10 is illustrated in FIG. 2. In particular, this embodiment generally comprises a shaped mass generally 25 positioned on the thrust element 20 and disposed between the main body 30 and the removable body contact member 28. In the illustrated embodiment, the shaped mass 25 is a multi-part arrangement with a frusto-conical shaped collar 26, an elongated sleeve 27 and tightening collar 29, as shown in FIGS. 3 and 4. It will be readily apparent to those skilled in the art, however, that the shaped mass 25 could be positioned on the thrust element 20 in other ways.

As best shown in FIGS. 3 and 4, the shaped mass 25 has collar 26 fixed to the body 30 by a set screw 31 and the sleeve portion 27 has an upper cylindrical portion and a lower portion that tapers inwardly from the sleeve cylindrical portion. Moreover, the shaped mass 25 is arranged on the thrust element 20 such that the sleeve portion 26 faces the first handle member 40 while the generally conical portion 27 faces the removable body contact member 28. It will be appreciated, however, that both the configuration and the orientation of the shaped mass 25 could be modified from the specific embodiment disclosed herein.

In keeping with an important aspect of the present invention, the preferred embodiment of the chiropractic adjusting instrument 10 is mechanically tuned to the natural frequency of most human spinal columns. More importantly, though, the frequency at which the chiropractic adjustment instrument 10 is mechanically tuned to can be adjusted—between a range of about 1 hertz to about 60 hertz—simply by moving the sleeve portion 27 downwardly with respect to collar 26 and rotating the sleeve to one of a number of preselected positions radially, and then moving the sleeve 27 upwardly to lock it in another position relative to the collar 26. In addition, once the chiropractic adjusting instrument 10 is "tuned" to the natural frequency of a particular spine at one of the preselected positions, the spine can then be excited at its natural frequency. Thus, in spinal manipulative therapy, the dynamic output response of the spine is maximized while the magnitude of the impact force delivered to the spine is minimized. This not only increases the overall effectiveness of spinal manipulative therapy but also significantly reduces the risk of vertebrae damage.

Figure 5:
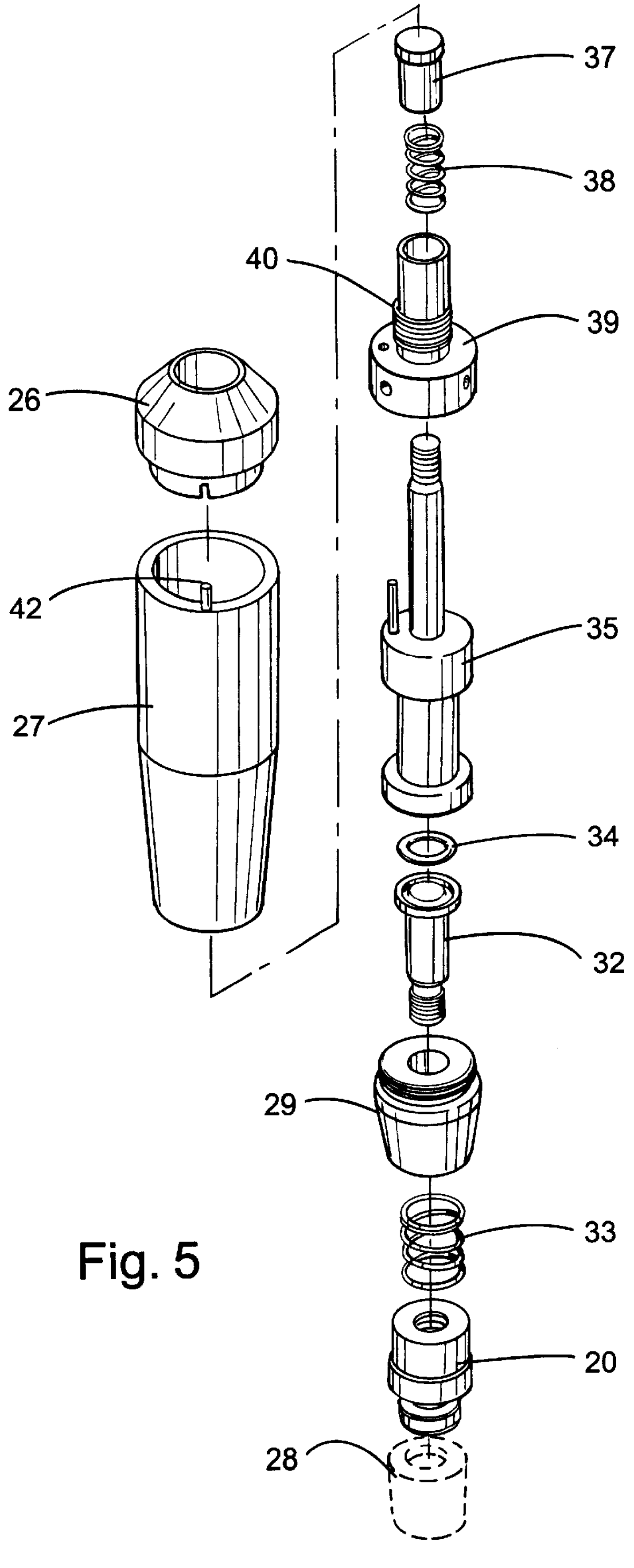
FIG. 5 is an exploded parts drawing of the shaped mass portion of the instrument.

As shown in FIGS. 3 and 5, the thrust member 20 threadably attaches to a plunger member 32 and with an intermediate spring 33 is held in place by lower collar 29 that threadably attaches to sleeve 27. The arrangement is such that the thrust member is pre-spring loaded so it must be pushed inwardly against a surface or body to position the upper head of the plunger 32 where it will be struck by piston 35 that receives the thrust from the trigger means within the body down through the trigger rod 37 when the handles are squeezed together. The trigger rod 37 is threadably attached to the upper threaded portion of piston 35 and a cushioning spring 38 is provided where the assembly is held by barrel 39 that is fixedly held by sleeve 27.

The threaded portion 40 of barrel 39 receives the internal threaded end of the main body 30 and rotation of the sleeve when in its pulled down position (FIG. 4) allows the mass 25 to be radially repositioned through piston 41 that acts through barrel 39. A pin 42 on the sleeve 27 (FIGS. 2 and 5) allows the sleeve to be positioned in a preselected number of preselected radial positions with respect to collar 26. In the present instance positions 1–3 have been shown where the instrument may be tuned to three different thrust frequencies. It will be appreciated that more or less of such positions may be provided. Preferably, the positions do provide the most common thrust frequencies used in a typical chiropractic practice. Since the sleeve 27 does "lock" into place at each of the selected positions, it is not apt to be rotated inadvertently thereby insuring a delivery of the same thrust frequency for a setting until it is intentionally reset.

In accordance with another feature of the invention, an O-ring resilient member 34 (FIG. 5) is seated on the top of plunger 32 so striking by the piston 35 is lightly cushioned and quieter in operation, thereby avoiding a metal to metal contact and its attendant sound.

What is claimed is:

1. An improved chiropractic adjusting instrument of the type having:

a thrust element including a shank portion and an outer end portion;

a removable body contact member positioned adjacent to the outer end portion of the thrust element;

a main body having a first end and a second end, the first end longitudinally slidably receiving the shank portion of the thrust element;

an end cap longitudinally slidably mounted on the second end of the main body;

a first handle member disposed on the main body;

a second handle member being squeezably disposed relative to the second handle member such that the first member moves toward the second handle member and the shank portion contracts to impart a single thrust to the thrust element when the first and second handle members are squeezed together;

a spring means disposed within the main body for propelling the thrust element outwardly; and a trigger means for actuating the spring means when the first and second handle members have been squeezed together a predetermined distance, wherein the improvement comprises, a preloaded body contact thrust member having a relative stiffness provided by said spring means normally urging the thrust member outwardly and which must be pressed against a body to re-position the thrust element against the action of said spring means that is propelling the thrust element outwardly for receiving and transferring the single thrust to the body when the handle members are squeezed together wherein the thrust member has a resilient O-ring means and its end receiving the thrust imparted from the handle squeezing action.

* * * * *